US00PP17821P2

(12) United States Plant Patent
Earman, Jr.

(10) Patent No.: US PP17,821 P2
(45) Date of Patent: Jun. 19, 2007

(54) HYBRID TEA ROSE PLANT NAMED 'WEKEARMAN'

(50) Latin Name: *Rosa hybrida*
Varietal Denomination: WEKearman

(75) Inventor: Ernest Earman, Jr., Alexandria, VA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 11/292,852

(22) Filed: Dec. 1, 2005

(51) Int. Cl.
*A01H 5/00* (2006.01)

(52) U.S. Cl. ..... Plt./139

(58) Field of Classification Search ..... Plt./139, Plt./130

See application file for complete search history.

*Primary Examiner*—Kent Bell
*Assistant Examiner*—Annette H Para
(74) *Attorney, Agent, or Firm*—Christie, Parker & Hale, LLP

(57) ABSTRACT

A new variety of Hybrid Tea rose suitable for garden decoration, having flowers of strawberry red coloration.

1 Drawing Sheet

Classification: The present invention relates to a new *Rosa hybrida* plant.

Variety denomination: The new plant has the varietal denomination 'WEKearman'.

BACKGROUND OF THE INVENTION

This invention relates to a new and distinct variety of Hybrid Tea Rose. It has as its seed parent the variety known as 'TOBone' (U.S. Plant Pat. No. 5,633) and as its pollen parent the variety known as 'KRIcarlo' (U.S. Plant Pat. No. 5,165).

SUMMARY OF THE INVENTION

Among the features which distinguish the new variety from other presently available and commercial rose cultivars known to the inventor are the following combination of characteristics: its sepal inner surfaces that blush red with age, its orangey red filaments, its anther coloration of blended yellow and purple and its long high centered partially open bloom. The plant has an upright moderately spreading growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKearman' may be asexually propagated by budding and grafting. The budding and grafting successfully occurred on the plant/rootstock *Rosa hybrida* cv. 'Dr. Huey'.

COMPARISON WITH PARENTS

The new rose may be distinguished from its seed parent, 'TOBone' by the following combination of characteristics: whereas 'WEKearman' bears medium size flowers (about 7.8 to about 11.3 cm in diameter) of strawberry red coloration, 'TOBone' bears significantly larger flowers (about 12.0 to about 13.0 cm in diameter) of brilliant red-purple coloration. The new variety is classified as a garden hybrid tea rose with blooms on the bush growing outdoors that generally last about four to five days, whereas the seed parent is classified as a cut flower hybrid tea rose with blooms on the bush growing outdoors that generally last for more than 15 days.

The new variety may be distinguished from its pollen parent, 'KRIcarlo' by the following combination of characteristics: whereas 'WEKearman' bears flowers of strawberry red coloration, 'KRIcarlo' bears flowers of warm orange pink coloration. The new variety has an upright moderately spreading tall growing habit (about 160 to about 185 cm in height), whereas the pollen parent has a bushy, upright to spreading significantly shorter growing habit.

COMPARISON WITH THE CLOSEST COMMERCIALLY AVAILABLE CULTIVAR

The closest commercially available cultivar to the new variety is the pollen parent 'KRIcarlo'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of October. Phenotypic expression may vary with environmental, cultural and climatic conditions, as well as differences in conditions of light and soil.

FLOWER

The new variety usually bears its flowers singly. Flowers are borne on strong medium length stems (about 30 to about 66 cm). Outdoors, the plant blooms abundantly and nearly continuously during the growing season. The flowers have a moderate tea fragrance.

BUD

The peduncle is about 5.1 to about 11.2 cm in length, of average to moderately heavy caliper (about 0.3 to about 0.5 cm in diameter), and usually erect and moderately stiff. It is rough, with few stipitate glands and some small prickles. Peduncle color is between 144A and 148A sometimes heavily suffused, especially on the side exposed to the sun, with between 187B and 183B.

Before the calyx breaks, the bud is about 0.9 to about 1.8 cm in diameter at the widest point, about 1.9 to about 2.6 cm in length, and pointed in shape. The surface of the bud bears many stout foliaceous appendages and some stipitate glands, usually with stout much cut foliaceous parts extending beyond the tip of the bud about ¾ or more of its length. Bud color is between 144A and 146B often heavily suffused, especially on the side exposed to the sun, with between 187B and 183B.

The sepals are about 3.0 to about 4.5 cm in length and about 0.7 to about 1.0 cm in width at the widest point. The outer surface color of the sepal is between 144A and 146B often heavily suffused, especially on the side exposed to the sun, with between 187B and 183B. The inner surface color of the sepal is between 137A and 144A and covered with fine wooly tomentum; sepal margins are lined with some stipitate glands and hairs. As the flower matures, the inner surface of the sepal often blushes over the entire surface with between 187A and 187B.

The receptacle of the flower is of somewhat short length (about 0.4 to about 0.6 cm) and moderately thin in caliper (about 0.6 to about 1.1 cm in diameter). The receptacle is cupped in form. Its surface is very smooth with thick fleshy walls. The receptacle color is between 144A and 146B.

As the petals open (after the calyx breaks), the bud is about 1.9 to about 2.7 cm in diameter at the widest point, about 2.7 to about 4.0 cm in length, and moderately ovoid in form. The color of the under and upper surfaces of the newly opened petals is between 187B and 53A sometimes moderately blushed near the petal edge with as dark as near 187A. At the point where the petal attaches, there is a small zone of between 1C and 154C.

BLOOM

When fully open, the bloom ranges from about 7.8 to about 11.3 cm in diameter. Petalage is double with about 24 to 32 petals and about 2 to 4 petaloids irregularly arranged. When partially open, the bloom form is high centered to somewhat cupped, and the petals are tightly spiraled to cupped with petal edges slightly reflexed outward. When fully open, the bloom form is cupped, and the petals are loosely cupped to undulated with petal edges moderately reflexed outward.

PETALS

The substance of the petals is very heavy and of moderately thick thickness, with upper surfaces moderately satiny and under surfaces slightly shiny. The petals are about 3.9 to about 5.5 cm in length and about 3.7 to about 6.7 cm in width at the widest point. Petal margins are entire.

The outer and inner petals are rounded in shape with rounded apices.

Petaloids are about 3.2 to about 3.9 cm in length and about 2.0 to about 3.5 cm in width at the widest point. Petaloids are irregularly shaped moderately obovate to somewhat oblanceolate with rounded apices.

NEWLY OPENED FLOWER

The under surface color of the outer, intermediate and inner petals is between 46A and 53B. At the point where the petal attaches, there is a very small zone of between 3B and 5B. The upper surface color of the outer, intermediate and inner petals is between 46A and 53C sometimes lightly blushed near the petal edge with between 187A and 187B. At the point where the petal attaches, there is a small zone of between 2C and 3C.

The under and upper surface color of the petaloids are similar in coloration to the upper and under surfaces of the intermediate and inner petals.

The general tonality of the newly opened flower is between 46A and 53C sometimes lightly blushed near the petal edge with between 187A and 187B.

THREE-DAY-OLD FLOWER

The under surface color of the outer, intermediate and inner petals is between 58B and 60B. At the point where the petal attaches, there is a very small zone of between 3D and 5D. The upper surface color of the outer, intermediate and inner petals is between 53C and 50A. At the point where the petal attaches, there is a small zone of near 3C.

The under and upper surface color of the petaloids are similar in coloration to the upper and under surfaces of the intermediate and inner petals.

The general tonality of the three-day-old flower is between 53C and 50A.

On the spent bloom, the petals usually drop off cleanly.

In October in Upland, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 200) and are arranged regularly about the pistils; a few are mixed with petaloids. The filaments are of medium length (about 0.5 to about 1.0 cm) most with anthers. Filaments are between 46A and 42C in color. The anthers are somewhat large for the class and all open approximately at the same time. Anther color is between 22B and 59C when immature and between 200A and 165C at maturity. Pollen is moderately abundant and between 19A and 20B in color.

FEMALE REPRODUCTIVE ORGANS

Pistils vary in number (average about 185). The styles are moderately uneven, somewhat long in length (about 0.5 to about 0.9 cm), somewhat thin to average in caliper and loosely separated to somewhat columnar. Stigma color is between 18D and 13D. Style color is between 2C and 3D often heavily suffused near the top with between 53A and 53B. Ovaries are usually all enclosed in the calyx.

Hips have not been observed on this variety when grown in Upland, Calif.

FOLIAGE

The compound leaves are usually comprised of three to seven leaflets and are borne abundantly. The five-leaflet leaves are about 9.9 to about 18.0 cm in length and about 7.0 to about 13.5 cm in width at the widest point, somewhat leathery to slightly crisp in texture, and moderately glossy in finish. The terminal leaflets are about 4.4 to about 7.9 cm in length and about 2.7 to about 5.2 cm in width at the widest point, shaped moderately oval to ovate with acute apices and rounded to somewhat acute bases. Their margins are usually simply serrate.

The upper surface color of the mature leaf is between 147A and 146A. The under surface color of the mature leaf is between 147B and 147C. The upper surface color of the young leaf is between 147A and 146B, usually heavily suffused with between 187A and 187B. The under surface color of the young leaf is between 138B and 146B, usually heavily suffused with between 187B and 183B.

The rachis is moderately light in caliper and rough. The upper side is moderately grooved with few hairs and stipitate glands on the edges of the grooves. The under side of the rachis is rough with very few hairs, some stipitate glands and few small prickles. The rachis color is between 145B and 146A, usually heavily suffused on the young leaves with between 187A and 187B.

The stipules are about 1.2 to about 1.9 cm in length and moderately wide (about 0.5 to about 0.8 cm) with somewhat short straight points that usually turn out at an angle of more than 45 degrees and somewhat recurve upward. The stipules color is between 145B and 146B, usually heavily suffused on the young leaves with between 187A and 187B.

The petiole is moderately light in caliper and rough. The upper side is moderately grooved with few hairs and stipitate glands on the edges of the grooves. The under side of the petiole is rough with very few hairs, some stipitate glands and few small prickles. The petiole is about 0.7 to about 3.2 cm in length and about 0.1 to about 0.2 cm in diameter at the widest point. The petiole color is between 145B and 146A usually heavily suffused on the young leaves with between 187A and 187B.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has an upright moderately spreading tall growing habit (about 160 to about 185 cm in height and about 50 to about 65 cm spread at the widest point), with full branching. It displays moderately vigorous growth and the canes are of somewhat light to medium caliper for the class.

The color of the major stems is between 146A and 146B. They bear many large prickles that are about 0.5 to about 0.7 cm in length. The large prickles are almost straight to angled slightly downward with a moderately short narrow oval base; prickle color is between 177B and 174B. The major stem bears few small prickles of similar shape and coloration.

The color of the branches is between 146C and 146A. They bear some large prickles which are of similar size and shape to the large prickles on the major stems; prickle color is between 160B and 162B sometimes moderately suffused with between 185C and 184D. The branches bear many small prickles of similar shape and coloration.

The color of the new shoots is between 146C and 146A often heavily suffused with between 187A and 187B. They bear many large prickles which are of similar size and shape to the large prickles on the major stems; prickle color is between 187A and 187B. The shoots bear many small prickles of similar shape and coloration.

I claim:

1. A new and distinct Hybrid Tea rose plant of the variety substantially as described and illustrated herein.

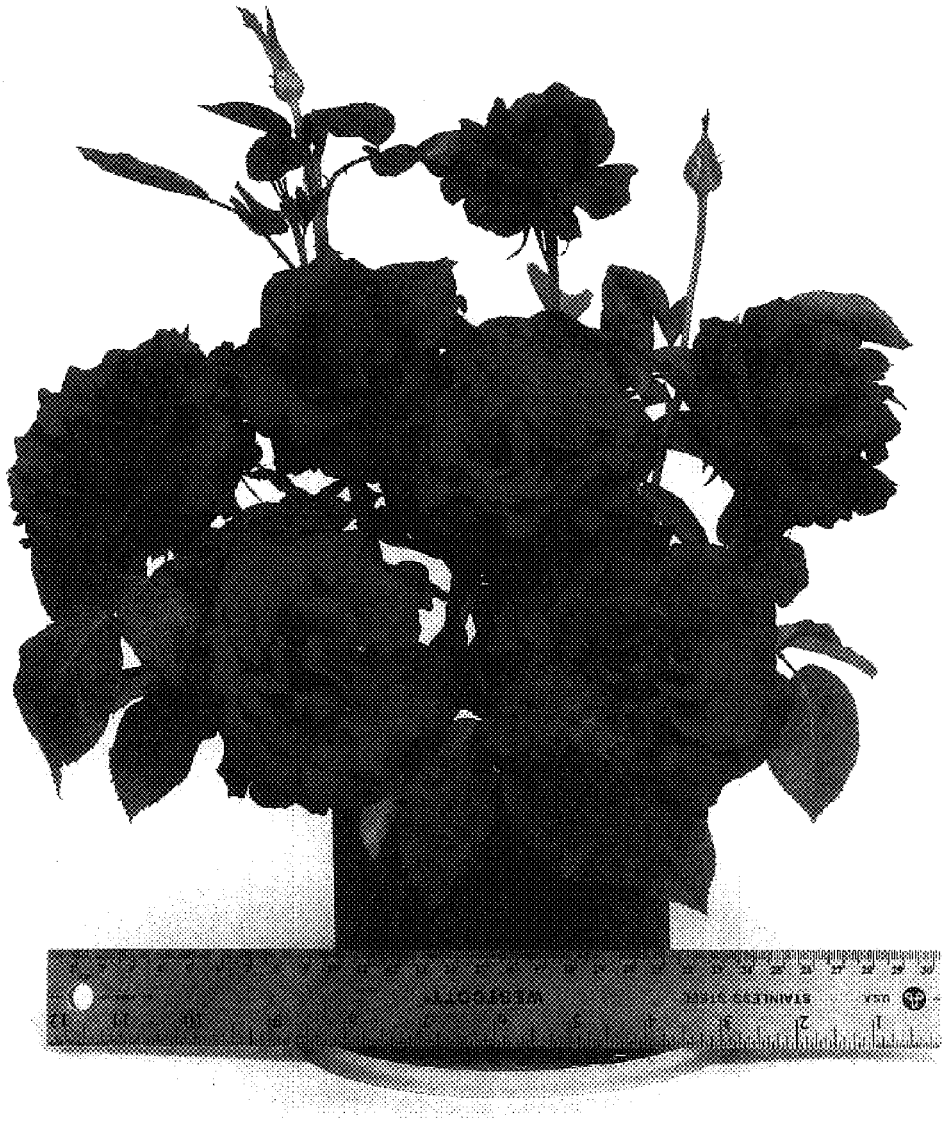

* * * * *